(12) United States Patent
Jensen et al.

(10) Patent No.: US 10,061,948 B2
(45) Date of Patent: Aug. 28, 2018

(54) SYSTEMS AND METHODS FOR EMULATING RFID TRANSPONDERS OF A PLURALITY OF MEDICAL DEVICES

(71) Applicant: COVIDIEN LP, Mansfield, MA (US)

(72) Inventors: Jeffrey L. Jensen, Boulder, CO (US); William Gary Paterson, Johnstown, CO (US); Erich M. Velandia, Erie, CO (US); Paul E. Ourada, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/806,339

(22) Filed: Jul. 22, 2015

(65) Prior Publication Data
US 2016/0055359 A1    Feb. 25, 2016

Related U.S. Application Data

(60) Provisional application No. 62/041,442, filed on Aug. 25, 2014.

(51) Int. Cl.

| | | |
|---|---|---|
| *G06K 7/10* | (2006.01) | |
| *A61B 90/00* | (2016.01) | |
| *G06K 7/00* | (2006.01) | |
| *G06K 19/07* | (2006.01) | |
| *A61B 90/98* | (2016.01) | |
| *G06Q 50/22* | (2018.01) | |
| *G06Q 10/08* | (2012.01) | |

(Continued)

(52) U.S. Cl.
CPC .......... *G06K 7/10366* (2013.01); *A61B 90/00* (2016.02); *A61B 90/98* (2016.02); *G06K 7/0095* (2013.01); *G06K 19/0725* (2013.01); *G06Q 50/22* (2013.01); *A61B 2018/00988* (2013.01); *G06K 2017/009* (2013.01); *G06Q 10/08* (2013.01)

(58) Field of Classification Search
CPC ............. G06Q 20/327; G06Q 20/3278; G06Q 20/3574; H04L 2209/88; H04L 67/12; H04W 4/14; G06K 7/10366; G06K 7/10039; G08B 13/2445
See application file for complete search history.

(56) References Cited

U.S. PATENT DOCUMENTS

| | | |
|---|---|---|
| 7,701,348 B2 | 4/2010 | Kim |
| 8,127,984 B2 | 3/2012 | Zatloukal et al. |

(Continued)

FOREIGN PATENT DOCUMENTS

WO    2006/063103 A2    6/2006

OTHER PUBLICATIONS

European Search Report for EP 15 17 8544 dated Feb. 4, 2016.

*Primary Examiner* — Kabir A Timory (57) ABSTRACT

A radio frequency identification (RFID) network is presented including a plurality of medical devices each including an RFID transponder and a single RFID transponder emulator configured to emulate functionality of each of the RFID transponders of the plurality of medical devices. The RFID network further includes a plurality of RFID interrogation devices configured to operatively communicate with the single RFID transponder emulator. The single RFID transponder emulator is used for development, testing, evaluation, and validation of each of the plurality of RFID interrogation devices.

18 Claims, 9 Drawing Sheets

(51) Int. Cl.
G06K 17/00 (2006.01)
A61B 18/00 (2006.01)

(56) References Cited

U.S. PATENT DOCUMENTS

| | | |
|---|---|---|
| 8,242,911 B2 | 8/2012 | Moore et al. |
| 8,373,544 B2 | 2/2013 | Pitt-Pladdy |
| 8,381,974 B2 | 2/2013 | Zatloukal et al. |
| 8,410,908 B2 | 4/2013 | Pendlebury et al. |
| 2006/0208859 A1* | 9/2006 | Hougen ............... G06K 7/0008 340/10.1 |
| 2007/0274242 A1 | 11/2007 | Lamacraft et al. |
| 2009/0184826 A1 | 7/2009 | Kim |
| 2010/0150348 A1* | 6/2010 | Fairbanks ............ H04L 9/0863 380/255 |
| 2012/0133490 A1* | 5/2012 | Downie ............ G06K 19/0717 340/10.1 |
| 2013/0176115 A1* | 7/2013 | Puleston ................ H04L 67/04 340/10.51 |
| 2013/0234832 A1 | 9/2013 | Manzi |
| 2013/0241701 A1 | 9/2013 | Almond et al. |
| 2014/0162721 A1 | 6/2014 | Zatloukal et al. |

\* cited by examiner

SYSTEMS AND METHODS FOR EMULATING RFID TRANSPONDERS OF A PLURALITY OF MEDICAL DEVICES

CROSS REFERENCE TO RELATED APPLICATION

This application claims priority to U.S. Provisional Patent Application No. 62/041,442 filed Aug. 25, 2014, the entire contents of which are hereby incorporated by reference.

BACKGROUND

1. Technical Field

The present disclosure relates to systems and methods for emulating a plurality of radio frequency identification (RFID) transponders with a single RFID transponder emulator.

2. Background of Related Art

Radio-frequency identification (RFID) is a wireless, non-contact use of radio-frequency electromagnetic fields to transfer data, for the purposes of automatically identifying and tracking transponders attached to objects. An RFID interrogator is used to wirelessly read, and optionally, write data stored in an RFID transponder that is physically attached to an object, such as a product, packaging, shipping container, and the like. The RFID transponder may include an integrated circuit (IC) for storing and processing data and for modulating and demodulating the RF signal, and an antenna coupled to the IC that enables the IC to exchange data between the transponder and interrogator. The RFID transponder may include read-only storage, which includes unalterable data, such as a unique identification code indelibly encoded during manufacturing. The RFID transponder may also include rewritable storage, in which the stored data may be changed and/or deleted. Typically, however, a read-write RFID transponder also contains read-only data, such as an indelible unique identification code, so that individual transponders can be uniquely identified.

RFID transponders may also be configured as secure (e.g., encrypted) RFID transponders, which include various security or protection features for preventing unauthorized reading and/or writing of the transponder. The secure RFID transponders may include a passcode stored in write-only storage, such that the passcode may be set or changed by a write operation, but may not be revealed by any read operation. In order for an interrogator to gain access to data in the secure RFID transponder, any read or write operations is preceded by a passcode exchange operation, in which the transponder compares the interrogator's passcode to the transponder's passcode. The secure RFID transponder normally indicates success or failure of passcode comparison in its response to the passcode operation.

RFID transponders may also be active or passive. Active RFID transponders include a power source, such as a battery, whereas passive RFID transponders are powered by energy derived from the RF interrogation signal. As a result, a passive RFID transponder typically has relatively modest processing and memory capabilities. Generally, but not exclusively, active RFID transponders are used in heavy industrial, municipal, and military applications, while passive RFID transponders are used in smaller devices such as tools, electronic devices and components, credit/debit cards, and the like. Active RFID transponders may also offer increased range over passive style transponders.

RFID transponders may be employed for a variety of purposes. One such purpose is to authenticate an accessory device (e.g., a surgical instrument) to determine whether the accessory device is suitable for use with another device (e.g., a console, an electrosurgical or microwave generator, etc.), which includes an RFID interrogator. Authentication may include generating, storing, and/or programming an authentication signature in the RFID transponder, which is attached or affixed to the accessory device. The authentication signature may be a secret identifier pertaining to the accessory device and is known or determinable only by the programmer of the RFID transponder, e.g., device manufacturer, vendor, user, etc. Thus, unless secured communication based on the authentication signature between the RFID interrogator and the secure RFID is established, usage of the devices may be prevented.

Due to variety of RFID transponders and interrogators, testing and deploying RFID systems is a costly and complex endeavor. Accordingly, there is a need for RFID apparatus, systems, and methods that provide for emulation of various RFID transponders.

SUMMARY

The present disclosure provides emulator RFID transponders, which may be used for emulating additional, multiple RFID transponders. In exemplary embodiments, an electronic emulator device may be used to emulate operation of an RFID transponder using a suitable electronic circuit and corresponding antenna. This electronic circuit may be integrated into or be part of the circuitry of the device itself (e.g., a medical device). The emulator RFID transponder may include data pertaining to multiple RFID transponders allowing for their emulation. The data describing various RFID transponders may then be made available to an RFID transponder interrogation device through an RFID circuit and corresponding antenna.

In accordance with aspects of the present disclosure, a system is presented. The system includes a plurality of medical devices each including a radio frequency identification (RFID) transponder and an RFID transponder emulator configured to emulate functionality of each of the RFID transponders of the plurality of medical devices.

The system may further include an RFID interrogation device configured to receive information emulated by the RFID transponder emulator.

The RFID transponders of each of the plurality of medical devices include data related to at least one of unique identifiers, digital signatures, authentication features, authorization features, anti-counterfeiting features, device usage management features, encrypted data, and unencrypted data.

The RFID transponder emulator includes an antenna, an analog front end (AFE), a processor, and a memory. The AFE imitates a behavior of an RFID transponder included in each of the RFID transponders of the plurality of medical devices. The processor processes information and the memory of the RFID interrogation device stores information received from the RFID transponder emulator via the AFE.

The RFID transponder emulator further includes a plurality of input controls for allowing selection of a mode from a plurality of modes of operation. The RFID transponder emulator may also include a display device for displaying the mode selected from the plurality of modes of operation.

In accordance with another exemplary embodiment, the system further includes an electrosurgical generator configured to receive and process information collected, processed, and stored on the RFID transponder emulator.

According to another aspect of the present disclosure, a radio frequency identification (RFID) network is presented.

The RFID network includes a plurality of medical devices each including an RFID transponder, a single RFID transponder emulator configured to emulate functionality of each of the RFID transponders of the plurality of medical devices, and a plurality of RFID interrogation devices configured to operatively communicate with the single RFID transponder emulator. The single RFID transponder emulator is used for development, testing, evaluation, and validation of each of the plurality of RFID interrogation devices.

According to another aspect of the present disclosure, a method of emulating a plurality of RFID transponders is presented. The method includes the steps of incorporating an RFID transponder of the plurality of RFID transponders with each of a plurality of medical devices, emulating functionality of each of the plurality of RFID transponders associated with a respective medical device of the plurality of medical devices via an RFID transponder emulator, and allowing a plurality of RFID interrogation devices to operatively communicate with the RFID transponder emulator, the RFID transponder emulator used for development, testing, evaluation, and validation of each of the plurality of RFID interrogation devices.

In accordance with further aspects of the present disclosure, a non-transitory computer-readable storage medium for storing computer executable instructions is presented. The non-transitory computer-readable storage medium includes a processor for executing the steps of incorporating an RFID transponder of the plurality of RFID transponders with each of a plurality of medical devices, emulating functionality of each of the plurality of RFID transponders associated with a respective medical device of the plurality of medical devices via an RFID transponder emulator, and allowing a plurality of RFID interrogation devices to operatively communicate with the RFID transponder emulator, the RFID transponder emulator used for development, testing, evaluation, and validation of each of the plurality of RFID interrogation devices.

Further scope of applicability of the present disclosure will become apparent from the detailed description given hereinafter. However, it should be understood that the detailed description and specific examples, while indicating illustrative embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the subject systems and methods are described herein with reference to the drawings wherein.

The figures depict preferred embodiments of the present disclosure for purposes of illustration only. One skilled in the art will readily recognize from the following detailed description that alternative embodiments of the structures and methods illustrated herein may be employed without departing from the principles of the present disclosure.

DETAILED DESCRIPTION

Reference will now be made in detail to embodiments of the present disclosure. While certain exemplary embodiments of the present disclosure will be described, it will be understood that it is not intended to limit the embodiments of the present disclosure to those described embodiments. To the contrary, it will be readily apparent to those skilled in this art that various modifications, rearrangements and substitutions may be made without departing from the spirit of the present disclosure. Further, reference to embodiments of the present disclosure is intended to cover alternatives, modifications, and equivalents as may be included within the spirit and scope of the embodiments of the present disclosure as defined by the appended claims.

Reference throughout this specification to "one embodiment," "an embodiment," or similar language denotes that a particular feature, structure, or characteristic described in connection with the embodiment is included in at least one embodiment of the present disclosure. Thus, appearances of the phrases "one embodiment," "an embodiment," and similar language throughout this specification may, but do not necessarily, all refer to the same embodiment, different embodiments, or component parts of the same or different illustrated disclosure. Additionally, reference to the term "an embodiment," or the like, for two or more features, elements, etc. does not mean that the features are related, dissimilar, the same, etc. The use of the term "an embodiment," or similar wording, is merely used to indicate optional features, which may or may not be part of the present disclosure as claimed. The independent embodiments are considered to be able to be combined in whole or in part one with another as the claims and/or art may direct, either directly or indirectly, implicitly or explicitly.

The terms "exemplary" as used herein denotes "serving as an example, instance, or illustration." Any embodiment described herein as "exemplary" is not necessarily to be construed as preferred or advantageous over other embodiments. The word "example" may be used interchangeably with the term "exemplary."

The terms "RFID," "RFID system," and "RFID network" as used herein denotes any interrogator/transponder combination that utilizes radio-frequency electromagnetic fields to transfer data, including, but not limited to traditional RFID systems, in which an RFID transponder supplies data to an RFID interrogator, near field communication (NFC) systems, and the like.

Likewise the terms "RFID transponder" or "transponder" as used herein should be understood, where the context permits, to include transponders and NFC devices in transponder-mode or data storage devices in similar form or with similar function. The term "RFID interrogator" or "interrogator" as used herein should be understood, where the context permits, to include transceivers and NFC devices in interrogator-mode or similar devices or devices with similar function.

RFID systems according to the present disclosure may operate over a wide range of frequencies, including low-frequency (LF) applications, high-frequency (HF) applications, and ultra-high-frequency applications (UHF). LF applications may operate from about 125 kHz to about 150 kHz. HF applications may operate from about 10 MHz to about 20 MHz, in embodiment about 13.56 MHz. UHF applications may operate from about 300 MHz to about 3 GHz. The range at which the RFID interrogator may communicate with the RFID transponder may be from a few centimeters to 10 meters or more based on various factors that affect RF wave transmission e.g., obstacles, frequency, signal strength, etc.

The present disclosure relates to radio-frequency identification (RFID) apparatus, systems, and methods for emulating a series of co-located RFID transponders in a single RFID transponder-emulator. The term "emulator" as used herein denotes hardware and/or software configured to duplicate functionality of one or more RFID transponders in another (e.g., emulator) RFID transponder, so that the emulated behavior closely resembles the behavior of the real RFID transponder. In exemplary embodiments, emulated behavior may include, but is not limited to, providing an air interface identical or at least compatible with the RFID transponders being emulated, with respect to various parameters (e.g., frequency, modulation, data rate and the like), providing same data content, and the like.

According to another aspect of the present disclosure, methods and systems are provided for emulating or mimicking or simulating or mirroring the functionality of a plurality of RFID transponders, including any Unique Identifiers (UIDs), digital signatures, authentication, authorization, anti-counterfeiting, and device usage management features, and encrypted or unencrypted data contained therein. The systems and methods of the present disclosure are used for a passive, HF RFID transponder emulator. However, the systems and methods could equally be used or applied, without limitation, to create emulators for LF and UHF passive and active RFID transponders, as well as active HF RFID transponders. One skilled in the art may contemplate a plurality of different RFID transponder emulators used in a plurality of different intended or desired or suitable applications.

The RFID system according to the present disclosure includes an RFID emulator configured to emulate a plurality of RFID transponders, the RFID emulator includes a transmitter, one or more data storage devices storing a plurality of identifiers corresponding to the RFID transponders, a controller for controlling the transmission simultaneously or sequentially of the identifiers in response to receipt of a signal from an interrogator through the transmitter.

The RFID emulator according to the present disclosure may implement multiple RFID transponders in a single device by emulating conformance to or compliance with collision detection or collision avoidance protocols in such a way that signals from apparently separate RFID devices, as received by the RFID interrogator, actually emanate from the same antenna on the same device, e.g., RFID emulator. Transponder emulations may be carried out within any suitable logic controller including, but not limited to, a microprocessor, microcontroller, reduced instruction set computer (RISC), state machine, and combinations thereof. These transponder emulations provide control of the functionality of the RFID emulator which is used to transmit data in response to receipt of an RF signal.

The RFID transponder according to the present disclosure, when in the vicinity or range of a suitable RF signal, demodulates that RF signal. The RFID transponder may also derive a power signal from the received RF signal. This is particularly the case where the RFID transponder is passive. The RFID transponder then responds to a received RF signal in accordance with any data and/or instructions contained within the RF signal and/or data stored within the transponder itself. The response may be either modulation of a new RF signal or the received RF signal, transmission of a new RF signal, and combinations thereof. Suitable RFID transponders include those covered by various international standards, such as ISO/IEC 14443, ISO/IEC 15693, and the like.

The RFID interrogator according to the present disclosure may transmit an RF signal, which may be modulated by an RFID interrogator in accordance with data and/or commands stored within the RFID interrogator. The RFID interrogator also receives RF signals, which may be previously generated modulated signals, new RF signals, or a new modulated RF signal. The RFID interrogator may also derive power from the received signals and may demodulate the received RF signal and respond to the received RF signal in accordance with any data and/or instructions contained within such an RF signal and/or data stored within the interrogator. Suitable RFID interrogators include those covered by various international standards, such as ISO/IEC 14443, ISO/IEC 15693, and the like.

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Figure 1:
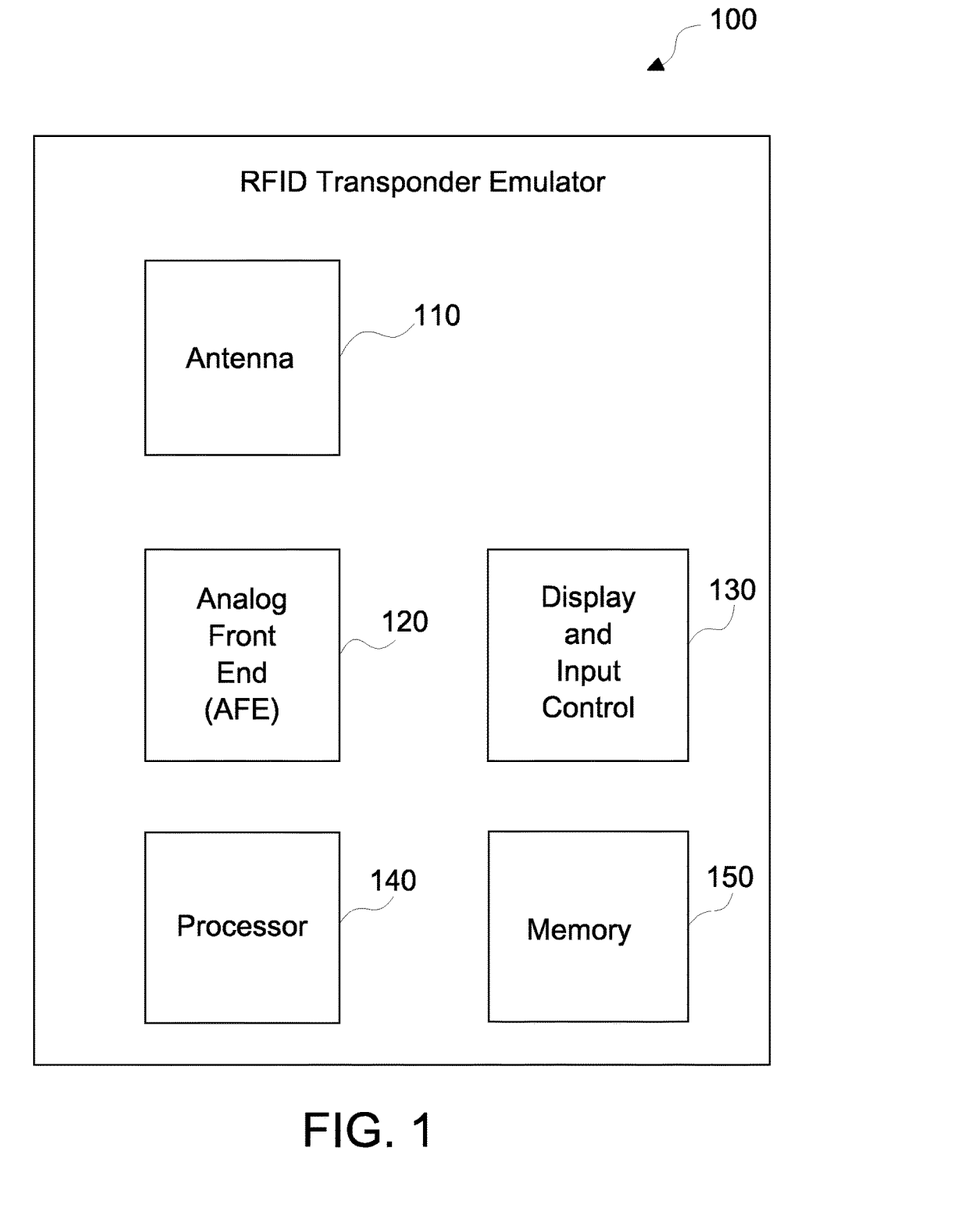
FIG. 1 is a schematic block diagram of an RFID transponder emulator, in accordance with embodiments of the present disclosure.

FIG. 1 is a schematic block diagram of an RFID transponder emulator 100, in accordance with embodiments of the present disclosure. The RFID transponder emulator 100 includes an antenna 110, an analog front end (AFE) 120, display and input control(s) 130, a processor 140, and a memory 150. The processor 140 is coupled to the memory 150 and the AFE 120.

Figure 2:
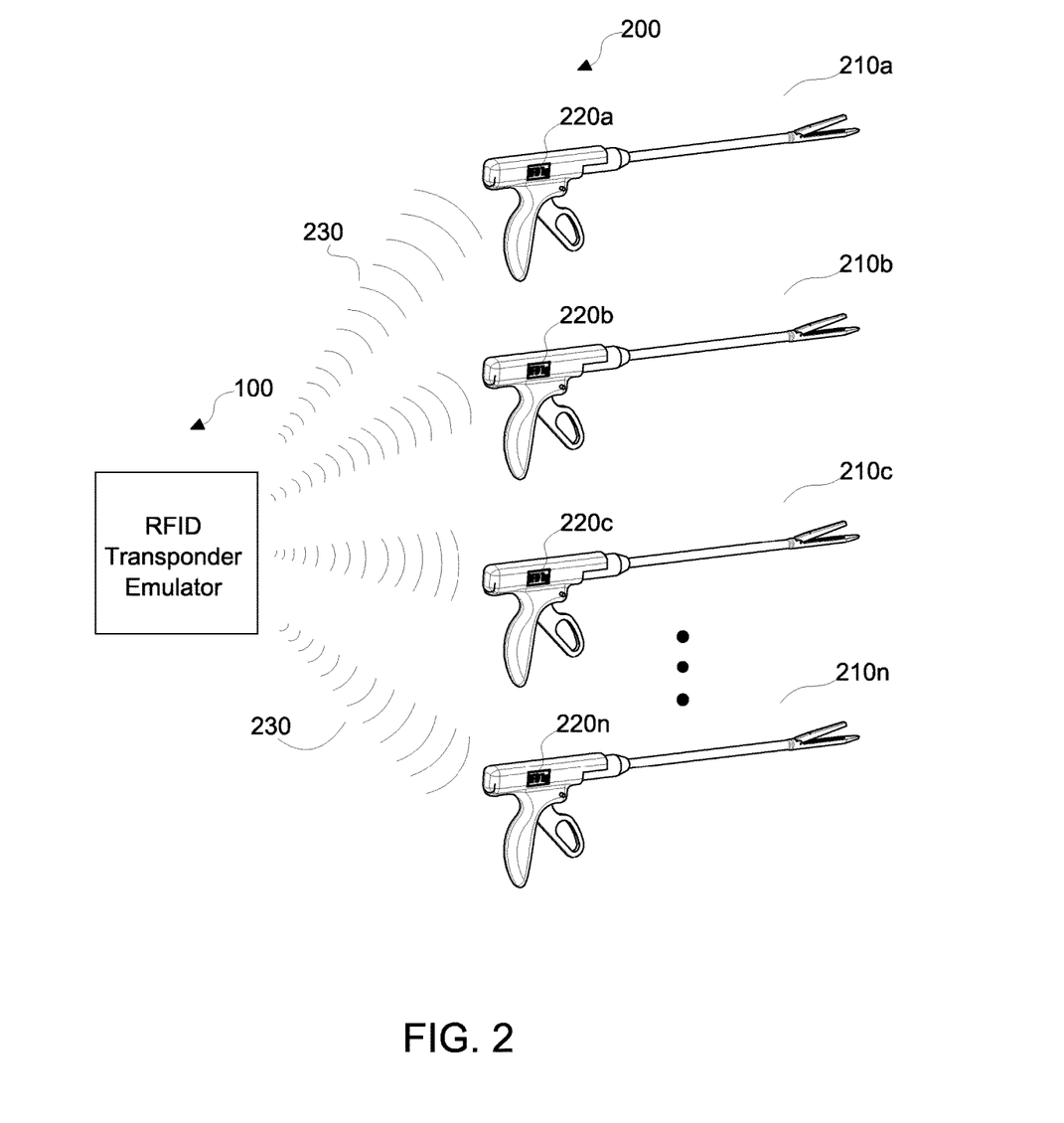
FIG. 2 is a system illustrating communication between the RFID transponder emulator of FIG. 1 with a plurality or RFID transponders of a plurality of medical devices, in accordance with an embodiment of the present disclosure.

The antenna 110 is capable of communicating with other antennas of other electronic devices or medical devices or surgical instruments (see FIG. 2). In other words, antenna 110 is configured to transmit signals to RFID interrogators disposed within other devices, e.g., medical devices.

The AFE 120 includes suitable RF signal processing circuitry that is configured to emulate, imitate, mirror, simulate, or otherwise mimic the radio frequency (RF) response of a passive or active RFID transponder, transceiver, transmitter, or receiver. The processor 140 is capable of receiving and processing information received from an RFID interrogator 310 (FIG. 3) via the AFE 120. The processor 140 is further capable of processing information received from one or more RFID interrogators and emulating RFID transponders.

The memory 150 may be any suitable non-transitory storage medium configured to store information received from one or more RFID interrogators 310 (see FIG. 3) and the data generated by the processor 140 during the course of processing information received or transmitted to the RFID interrogators 310 via an emulating circuit (not shown) in the AFE 120.

The memory 150 is provided for storing a plurality of data sets, wherein each data set defines the properties of an RFID transponder. This refers to the air interface parameters, as well as the actual data payload of such an RFID transponder. These air interface properties may include operating frequency, transmission rate, supported functionality, modulation form and other parameters associated with the air interface as described in further detail below with respect to FIG. 4.

Emulation data (e.g., RFID transponder profiles) may be uploaded into the RFID transponder emulator 100 using any suitable communication protocols either wired or wireless, e.g., RFID. In exemplary embodiments, the display and input control(s) 130 may be used to manage data entry and RFID transponder profiles.

With reference to FIG. 2, a system 200 for uploading data from a plurality of RFID transponders 220a-n of a plurality of medical devices 210a-n into the RFID transponder emulator 100 is shown. In the system 200, the RFID transponder emulator 100 wirelessly communicates with a plurality of RFID transponders 220a-n of surgical instruments 210a-n, respectively. In other words, the RFID transponder emulator 100 sends signals 230 to each of the plurality of RFID transponders 220a-n. The RFID transponders 220a-n may be attached or affixed to any portion of the surgical instrument 210a-n. One skilled in the art may contemplate communication with any type of medical device within a medical facility or hospital or any remote location. After communication is established, the RFID transponder emulator 100 downloads data from the RFID transponders 220a-n for emulation. Of course this is merely an exemplary system and building an RFID reader into the emulator to read RFID tags in medical devices is merely optional. It is contemplated that the RFID reader and the emulator are separate and distinct devices, such that data is created for the medical devices on, for example, a computer. Such data created on a computer may then be downloaded, for example, to the emulator.

Figure 3:
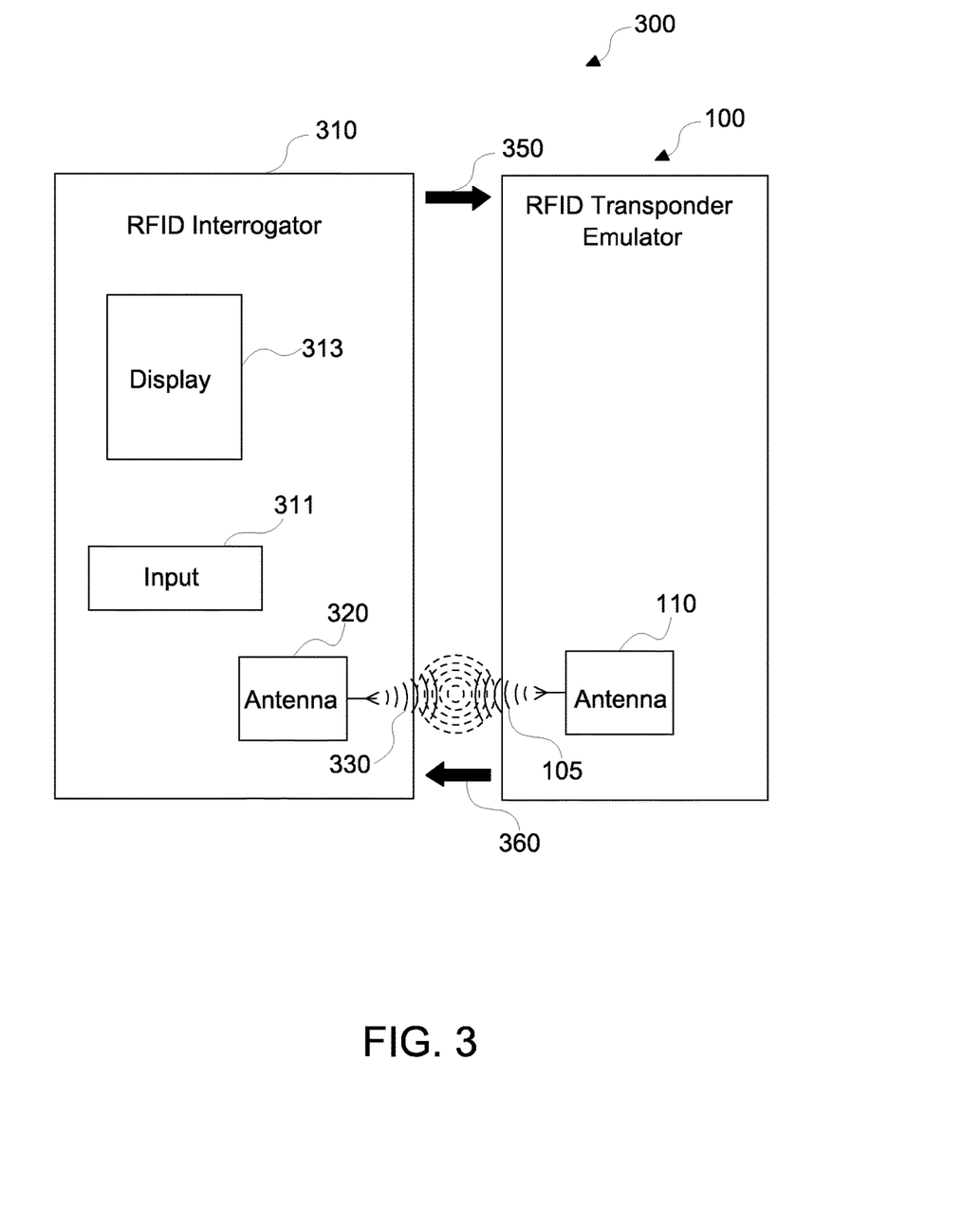
FIG. 3 is a system illustrating communication between the RFID transponder emulator of FIG. 1 and an RFID transponder interrogator (or interrogator), in accordance with an embodiment of the present disclosure.

FIG. 3 shows a system 300 illustrating communication between the RFID transponder 100 emulator of FIG. 1 and an RFID transponder interrogator 310, in accordance with an embodiment of the present disclosure. The RFID transponder interrogator 310 wirelessly communicates with the RFID transponder emulator 100. The RFID transponder interrogator 310 may include an input means 311 and a display means 313. The RFID transponder interrogator 310 also includes an antenna 320 configured to communicate (e.g., transmit signals 330) with the antenna 110 of the RFID transponder emulator 100 (e.g., antenna 110 sends signals 105). The RFID transponder interrogator 310 transmits data 350 to the RFID transponder emulator 100, whereas the RFID transponder emulator 100 transmits data 360 to the RFID transponder interrogator 310.

Figure 4:
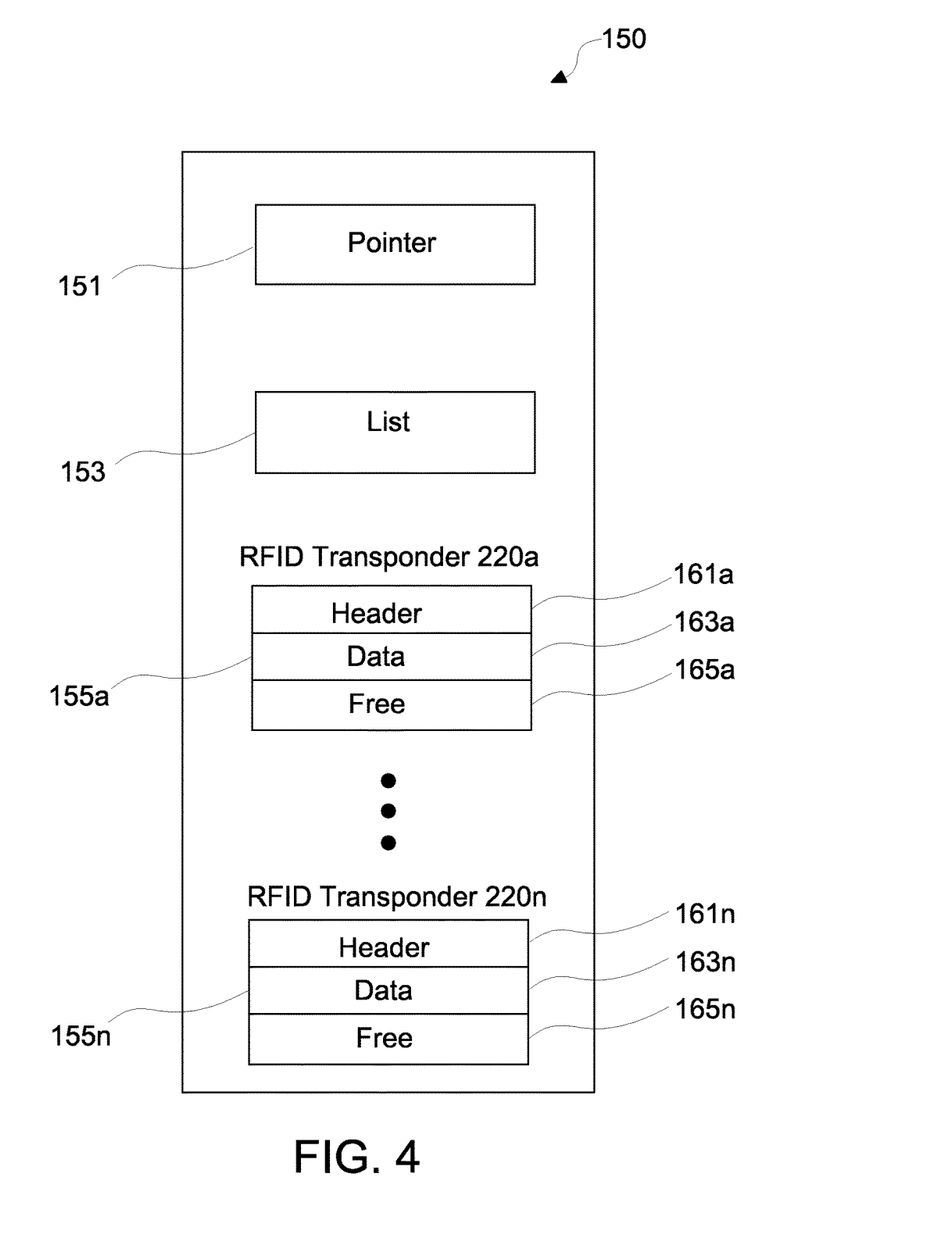
FIG. 4 is a schematic view of the structure of the memory contents of the RFID emulator of FIG. 1, in accordance with an embodiment of the present disclosure.

FIG. 4 is a schematic view of the structure of the memory contents of the memory 150 of the RFID emulator 100 of FIG. 1, in accordance with an embodiment of the present disclosure. The memory 150 stores a plurality of data sets 155a-155n corresponding to data stored within each of the plurality of RFID transponders 220a-220n (e.g., RFID transponders 220a-220d). In exemplary embodiments, the memory 150 may store any number of data sets referring to any number of RFID transponders 220a-220n, etc. The memory 150 also stores a list 153 (e.g., look-up table), which includes an ordered list of the stored data sets 155a-155n. In exemplary embodiments, the list 153 may include an indicator (e.g., an identifier) for each RFID transponder 220a-220n as well as the starting position and size of the data sets 155a-155n within the memory 150, which may be used as parameters for accessing respective data for configuring the RFID transponder emulator 100. The list 153 may also include management information enabling the processor 140 (FIG. 1) for handling the data sets 155a-155n.

Data sets 155a-n may also include a header section 161a-n, a body section 163a-n, and, optionally, a free section 165a-n, respectively. To avoid unnecessary detail, only the header section 161, the body section 163, and the free section 165 are described below. The header section 161 may define properties of the air interfaces of the corresponding RFID transponder, e.g., RFID transponder 220a, including but not limited to, various parameters like frequency, modulation, data rate, used protocol and the like. The data section 163 may store data content regarding the surgical instruments or medical devices to which the RFID transponder 220a is coupled. The free sections 165 may be used to store any additional data regarding the RFID transponders 220a, e.g., commentary, notes, etc. In exemplary embodiments, the data section 163 and free section 165 are rewritable, such as in case the RFID transponders 220a include rewriteable storage.

The memory 150 also includes a pointer 151, which indicates which of the data sets 155a-n is to be presented to RFID interrogator 310 upon interrogation of the RFID emulator transponder 100. The pointer 151 is set to refer to the one of the data sets 155a-n, making one the RFID transponders 220a-220n as the "active transponder," each time the emulating circuit (e.g., AFE 120) is activated by a read operation. In this way, the RFID emulator transponder 100 may utilize any of the data sets 155a-n to emulate any of the available RFID transponders 220a-n. Therefore, the pointer 151 aids in accessing/storing the correct information of each medical device associated with each respective RFID transponder 220a-220n. Thus, it is ensured that the RFID transponder data/information is properly associated with each respective medical device 210a-n. In an exemplary embodiment, list 153 is used in conjunction with pointer 151 in order to locate the data sets 150a-n that are to be accessed.

During operation of the RFID emulator transponder 100, the RFID interrogator 310 accesses data from the memory 150 of the RFID transponder emulator 100. In particular, the processor 140 of the RFID transponder emulator 100, upon an interrogation, configures the emulator circuit of the AFE 120 according to one of the data sets 150a-n stored in memory 150. In order to perform this action, the processor 140 reads the pointer 151 stored in the memory 150, which refers to one of the data sets 155a-n in the memory 150. The processor 140 is thus enabled to access the respective data set 155a-n, in order to use the properties defined by the data set 155a-n to configure the emulator circuit of the AFE 120.

According to an embodiment of the present disclosure, the RFID emulator transponder 100 may be reprogrammed by the user to modify the data stored in the memory 150, e.g., reset the pointer 151, re-arrange the succession of data sets 155a-n, and the like. In exemplary embodiments, the user may select one of the data sets 155a-n, and then move the selected data set to a desired position within the list 153, or set the pointer 151 to refer to a particular data set 155a-n. Other possible ways of achieving such list arranging/re-setting of the pointer 151 are readily available to a person of ordinary skill in the art.

Figure 5:
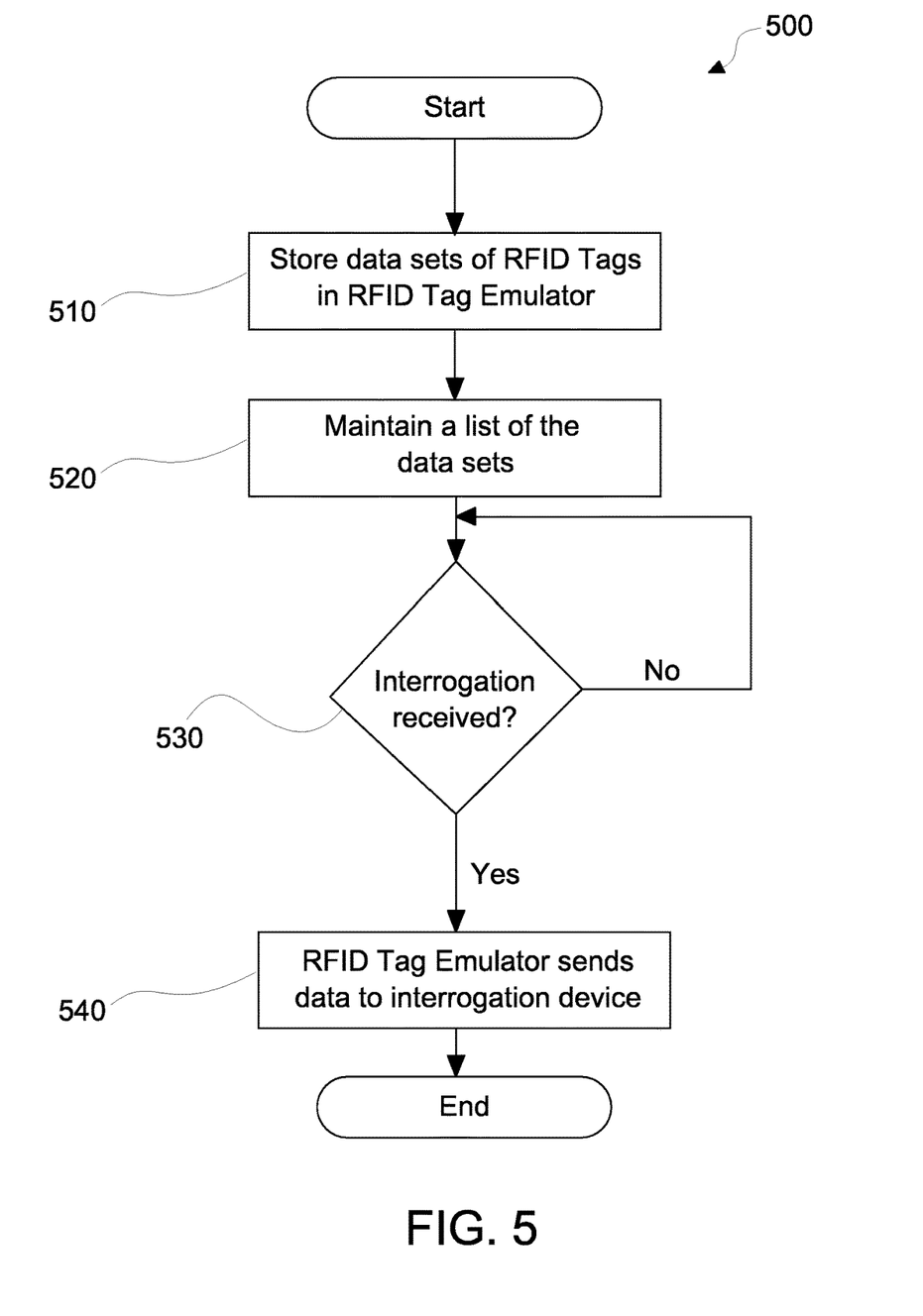
FIG. 5 is a flowchart illustrating a method of communication between the RFID transponder emulator and the RFID transponder interrogator, in accordance with an embodiment of the present disclosure.

FIG. 5 shows a flowchart 500 of a method for communication between the RFID transponder emulator 100 and the RFID interrogator 310, in accordance with an embodiment of the present disclosure. In step 510, data sets 155a-n of RFID transponders 220a-n, respectively, are stored in the memory 150 of the RFID emulator transponder 100. In step 520, the list 153 of the data sets 155a-n is maintained. In step 530, it is determined whether an interrogation is received from the RFID interrogator 310. If so, the process proceeds to step 540, in which the RFID transponder emulator 100 sends data to the RFID interrogator 310. The process then ends for the first cycle or first iteration. If interrogation is sent/received, the process reverts to step 530. In exemplary embodiments, the process may be a continuous iterative process, in which the steps may repeat for a number cycles or iterations, where the steps are constantly repeated.

Figure 6:
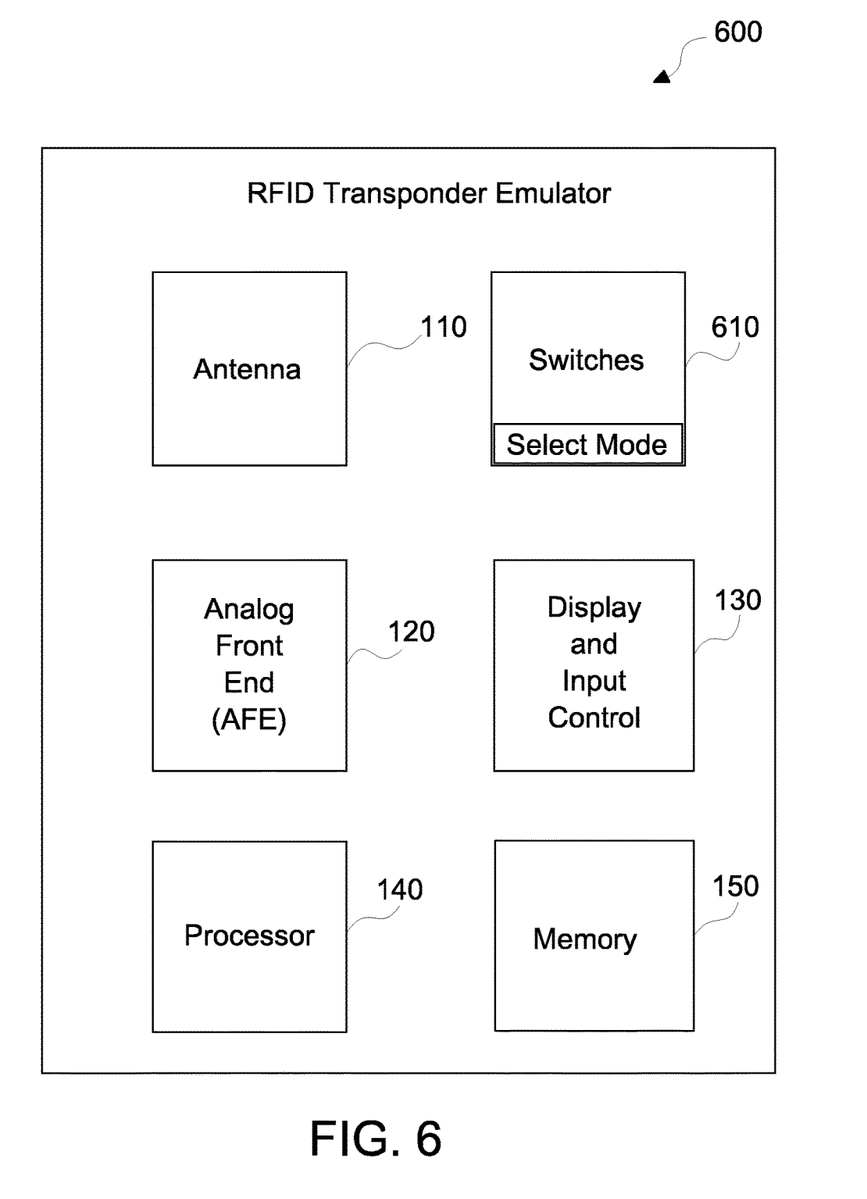
FIG. 6 is a schematic block diagram of an RFID transponder emulator including a plurality of switches or input controls, in accordance with an embodiment of the present disclosure.

FIG. 6 is a schematic block diagram of another embodiment of an RFID transponder emulator 600 including a plurality of switches or input controls 610, in accordance with an embodiment of the present disclosure. The RFID transponder emulator 600 is similar to the RFID transponder emulator 100 of FIG. 1. Similar elements described in FIG. 1 will not be described in this section. In contrast to FIG. 1, the RFID transponder emulator 600 of FIG. 6 includes switches 610. The RFID transponder emulator 600 may include one or more switches or input controls 610 in order to allow a user to select a mode of operation. A mode of operation may include a selective emulation mode of some or all of the RFID transponders 220a-n (FIGS. 2 and 4). Another mode of operation may include a sequential emulation of some or all of the RFID transponders 220a-n. The modes of operation may also include random modes of operation.

In exemplary embodiments, a user may select a mode of operation for the RFID transponder emulator 100 based on specific usage scenarios of the surgical instruments 210a-n, e.g., usage for specified time periods, specific procedures, etc. In exemplary embodiments, the mode of operation may be selected based on a specific practitioner who used a number of surgical instruments for a predetermined time period (e.g., the last three months). Further details of this process are described below. A plurality of different scenarios for selecting different emulation modes or modes of operation taking into account a number of different variables and/or parameters are also envisioned by the present disclosure.

Figure 7:
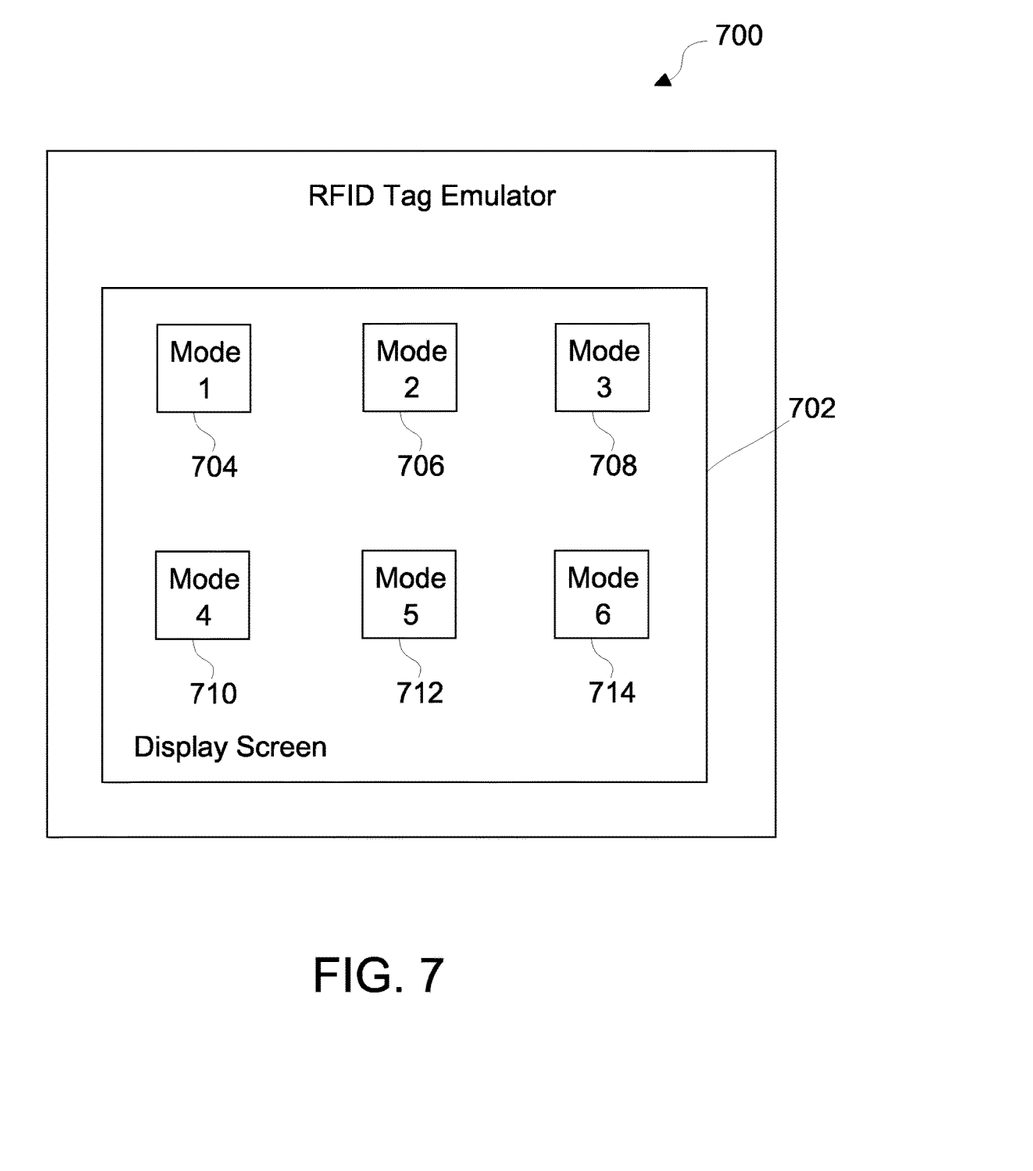
FIG. 7 is a schematic block diagram of an RFID transponder emulator including a display screen for displaying a plurality of modes of operation, according to one aspect of the present disclosure.

FIG. 7 illustrates a schematic block diagram of another embodiment of an RFID transponder emulator 700 including a display screen 702 that displays various modes of operation. In exemplary embodiments, display screen 702 may depict a plurality of modes of operation to the user, such as a first mode button 704, a second mode button 706, a third mode button 708, a fourth mode button 710, a fifth mode button 712, and a sixth mode button 714. The modes of operations may incorporate a number of different types of information. In exemplary embodiments, modes may include modifying any parameter of the RFID transponder being emulated, such as manufacturer, model number, information/data related to status and error conditions, parameters monitored by the one or more surgical instruments 210a-n, data transmitted and/or received by one or more RFID transponders 220a-n of one or more surgical instruments 210a-n, information/data related to the RFID transponder interrogator 310, and the like. In exemplary embodiments, emulation modes selected could also include password protection, locked data blocks, read only operations, destroy/privacy modes, etc.

With continued reference to FIGS. 6 and 7, a mode may refer to one or more parameters monitored and/or sensed by one or more of the medical devices 210a-n. A mode may also refer to one or more monitored and/or sensed parameters of one of the medical devices 210a-n. A mode may refer to a single device or to a group of medical devices 210a-n, which may include one specific type of medical instrument or a plurality of different medical instruments. The group of medical devices 210a-n may also refer to different instruments located in one particular area of a medical facility or in multiple areas of a particular medical facility. A mode may further refer to one surgical procedure or a plurality of surgical procedures or to a plurality of surgical procedures performed via a plurality of medical devices 210a-n. A mode may also refer to a practitioner using one instrument, a single doctor using multiple instruments, a single doctor using multiple instruments in multiple areas of a medical facility, or to multiple doctors using multiple instruments in multiple areas (or a single area) of a medical facility. It is envisioned that any combination of the above modes may be performed. Thus, the modes shown in FIG. 7 may be at least doctor-specific or area-specific or instrument-specific.

In additional embodiments, a mode may be patient-specific. The mode may relate to one or more patients connected to a plurality of different medical devices. A mode may also relate to RFID transponders 220a-n of a plurality of medical devices 210a-n used on a single patient or in a single procedure. The mode may also be procedure or condition-specific, such that RFID transponders 220a-n related to medical devices 210a-n used to treat specific conditions may be selected based on a mode. Also, the mode may be time-specific, such that the RFID transponders related to medical devices used during a specified time period may be selected based on a mode. It is envisioned any number of different combinations of the above modes may be used to configure the RFID transponder emulator 700.

Thus, RFID transponder information/data may be organized and categorized according to several different variables (e.g., time, patient, doctor, parameter sensed/monitored, devices, diseases, areas, procedures, etc.). Therefore, several different groupings of data/information may be performed as a result of emulating a plurality of RFID transponders attached or affixed to a plurality of medical devices within one or more medical facilities. The above-described different modes may be displayed on display screen 702 of FIG. 7.

It is also contemplated that a user may be able to create unique modes based on a number of desired applications. In exemplary embodiments, a user may be permitted to select one or more variables to create a unique mode (with a unique combination of variables and/or parameters) to be displayed on the RFID transponder emulator 700. Custom or customizable modes may be stored for each unique user and may be accessible to other users of the RFID transponder emulator. The custom modes may be created by providing a user with a list of variables and/or parameters to choose from. These lists may be updated in real-time as information/data associated with the medical devices is updated in real-time. This allows for medical devices, which receive software updates incorporating new information/data to upload into the existing lists for updating purposes of the RFID transponder emulator 700.

Figure 8:
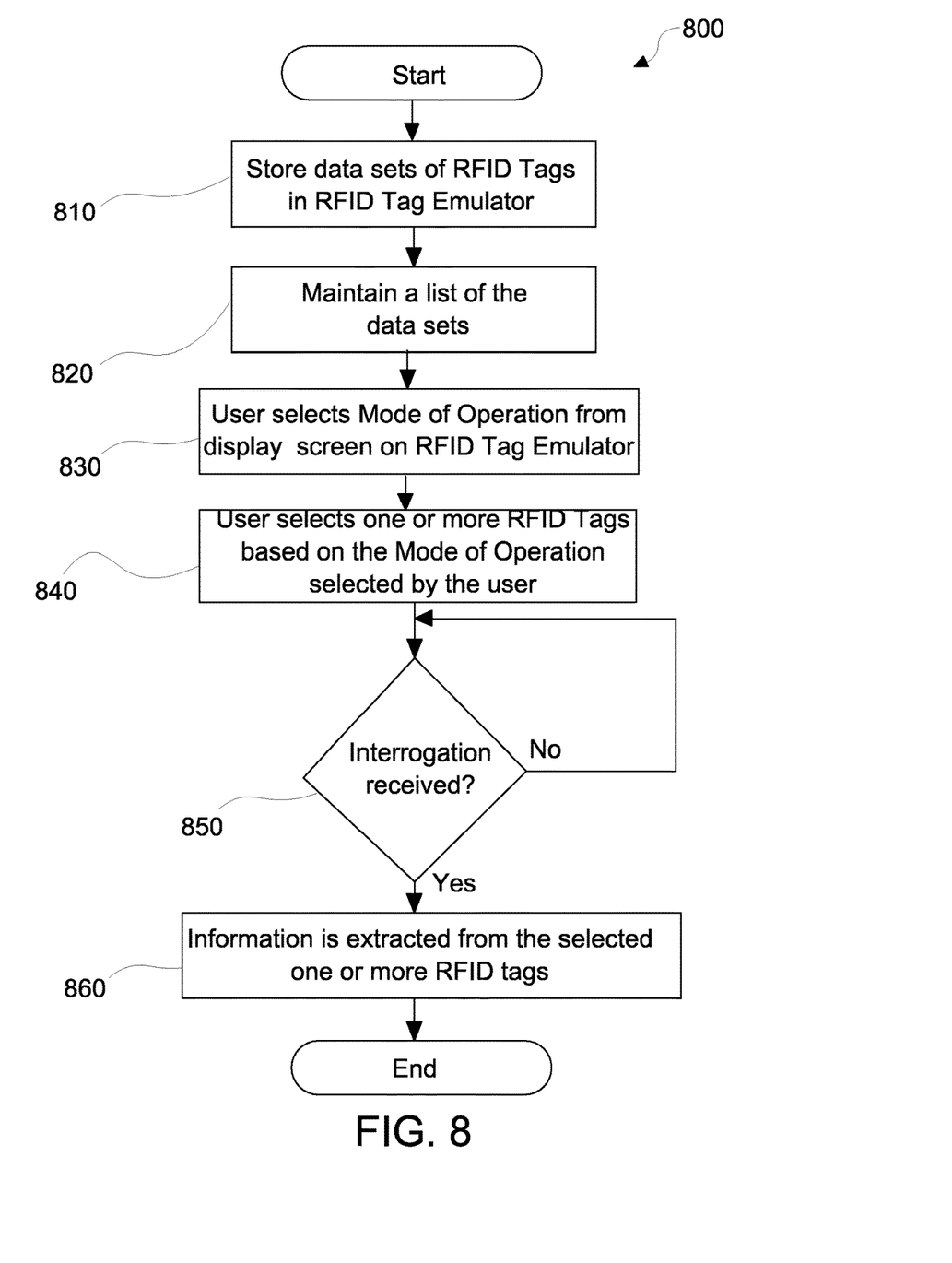
FIG. 8 is a flowchart illustrating a method of selecting a mode from a plurality of modes of operation via the display screen depicted in FIG. 7, according to one aspect of the present disclosure.

FIG. 8 is a flowchart 800 illustrating a method for selecting a mode from a plurality of modes of operation via the display screen depicted in FIG. 7, according to one aspect of the present disclosure. Although the method is described with respect to the RFID transponder emulator 700, it is also applicable to the RFID transponder emulator 100. In step 810, the data sets 155a-n of the RFID transponder emulator 700 are stored. In step 820, the list 153 of the data sets 155a-n is maintained.

In step 830, the user is permitted to select a mode of operation from the display screen 702 of the RFID transponder emulator 700. In step 840, the user is permitted to select one or more RFID transponders 220a-n based on the mode of operation. In step 850, it is determined whether an interrogation from the RFID transponder interrogator 310 is received. If "no," the process returns to step 840. If "yes," the process proceeds to step 860, where the information is extracted from the selected one or more RFID transponders 220a-n. In exemplary embodiments, the process may be a continuous iterative process, in which the steps may repeat for a number cycles or iterations, where the steps are constantly repeated.

Figure 9:
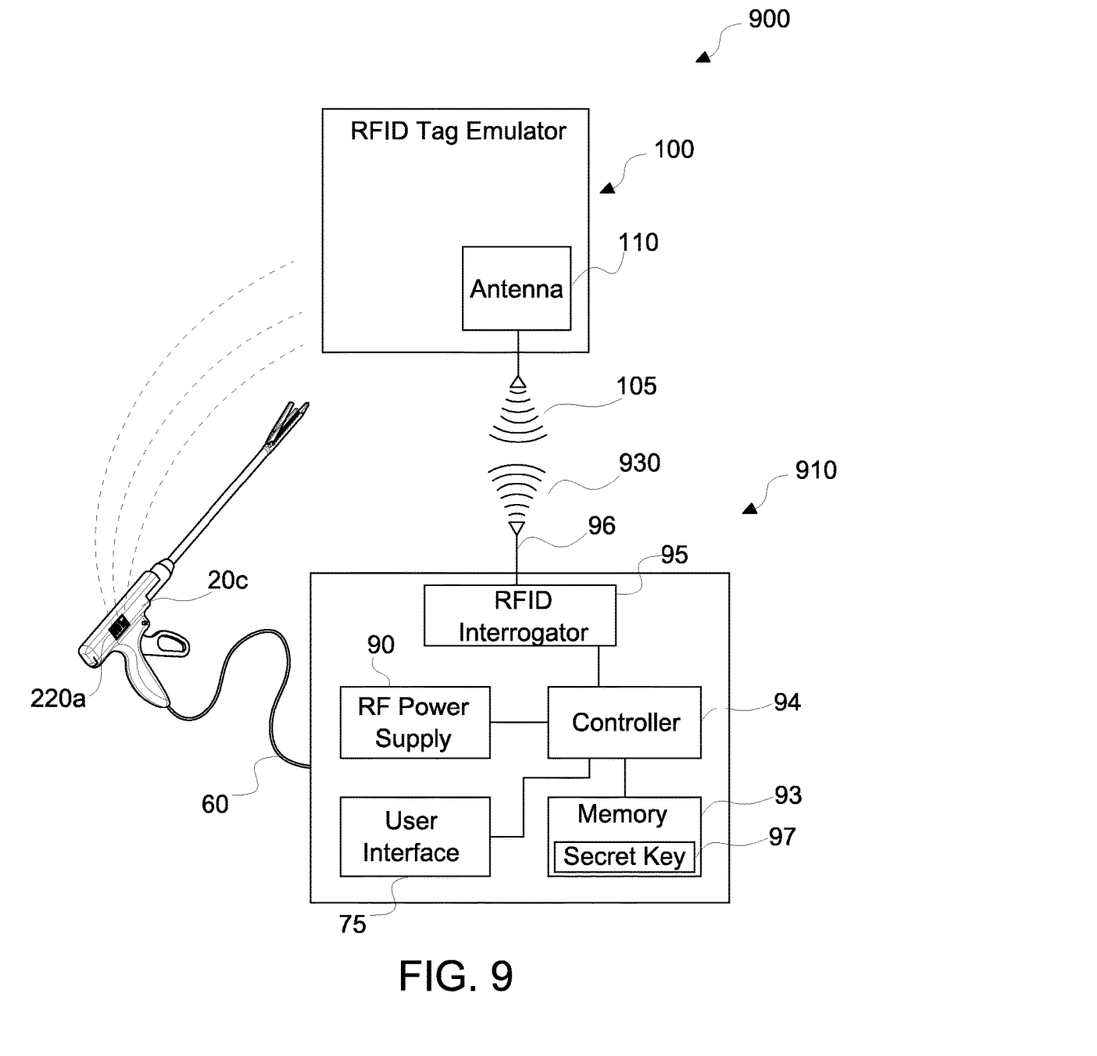
FIG. 9 is a system illustrating communication between the RFID transponder emulator of FIG. 1 and an RFID interrogator (interrogator) of an electrosurgical generator, according to one aspect of the present disclosure.

FIG. 9 illustrates a system 900 including the RFID transponder emulator 100 of FIG. 1 communicating with an electrosurgical generator 910 via signals 105, 930. The electrosurgical generator 910 includes an RFID transponder interrogator 95, an RF power supply 90, a controller 94, a user interface 75, and a memory 93 having a key 97. The electrosurgical generator 910 is connected via, for example, a cable 60 to a surgical instrument 20c. The surgical instrument 20c includes the RFID transponder emulator 100. Of course, one skilled in the art may envision the RFID transponder emulator 100 of FIG. 1 communicating with any medical device or general device (not just an electrosurgical generator) via signals 105, 930. Thus, the RFID interrogator 95 may be associated with or incorporated thereon or within any type of medical device or general device (not just an electrosurgical generator).

The controller 94 is in operable communication with RF source 90 that is configured to deliver electrosurgical energy to instrument 20c. In embodiments, wireless communication is also envisioned. Controller 94 is in operable communication with RFID interrogator 95, and memory 93. Memory 93 includes a copy of a key 97. In some embodiments, key 97 may be stored in memory 93 in encrypted or encoded form to hinder reverse-engineering and/or discovery of key 97 by an attacker. Key 97 may be a secret key when symmetrical authentication is used or key 97 may be a public/private key pair if asymmetrical authentication is used, such as if ECDSA is used.

RFID interrogator 95 also includes an antenna 96 that enables generator 910 to communicate effectively with RFID transponder emulator 100. Generator 910 includes a user interface 75 in operable communication with controller 94 that is configured to display operational data and provide audible tones to a user, and to accept user inputs.

RF source 90 is configured to selectively deliver electrosurgical energy in response to one or more control signals received from controller unit 94. Controller unit 94 is configured to receive user input signals from user interface 75 and is configured to receive authentication signals from RFID interrogator 95.

It is contemplated that the key 97 is stored in each device configured to perform authentication in accordance with the present disclosure. For example, the key 97 may be stored within memory 93 of generator 910, within RFID interrogator 95, as can be appreciated by the skilled artisan.

Therefore, in accordance with FIGS. 1-9, the RFID transponder emulator 100 is capable of transmitting information/data contained in a plurality of RFID transponders 220a-n attached or affixed to a plurality of surgical instruments 210a-n (or other medical devices) to the RFID transponder interrogator 310 without the express need to have a plurality of RFID transponders containing independent sets of data or unique identifiers (UIDs). As a result, a single RFID transponder emulator 100 may be used to select one or more of a plurality of data sets and UIDs, and emulate, imitate, mirror, simulate, or otherwise mimic the behavior of a wide range of RFID transponders for testing, evaluation, validation, or other use in RFID interrogator development. Similarly, this system described herein allows a single emulator to provide data sets and/or UIDs for multiple medical devices for use with, for example, an electrosurgical generator, as described above with reference to FIG. 9. Of course, one skilled in the art may envision the single emulator providing data sets and/or UIDs for use with any type of medical device or general device (not just an electrosurgical generator).

The RFID transponder emulator of the present disclosure is capable of mimicking or emulating or mirroring or simulating the behavior of multiple RFID communication protocols, such as ISO 15693 and ISO 14443 A/B, without the need to have an actual RFID transponder of each type present. This enables a single emulator to be used for testing, evaluation, or use with a plurality of RFID transponder interrogators capable of communicating via a single or multiple protocols.

The RFID transponder emulator may also be used to simulate the behavior of RFID transponders that are not commercially available or not yet in production by the RFID transponder integrated circuit (IC) vendors, by modifying the instruction sequence of the processor or the hardware in the state machine, along with the memory contents. Thus, the RFID transponder emulator may simulate the behavior of an RFID transponder IC with larger memory capacity, different commands, passcodes, control registers, larger register sets, and authentication or anti-counterfeiting schemes. This allows for the development of RFID interrogators and host system software for RFID transponders not yet available for use.

Some of the advantages of the present disclosure include the use of a single RFID transponder emulator for development, testing, evaluation, and validation of RFID transponder interrogators and software for interfacing with a variety of RFID transponder UIDs, encrypted and unencrypted data sets, digital signatures, authentication, authorization, anti-counterfeiting schemes and device usage management features, and combinations thereof. This allows for subsequent incorporation of these features into electrosurgical generators or other medical devices utilizing RFID transponders in a shorter timeframe. Another advantage is that the RFID emulator may function in place of an existing RFID transponder in a medical device, such as a surgical instrument, for example, in a case where the RFID transponder in the medical device is non-functional or inoperable and cannot be read, for example, by an electrosurgical generator. This would allow the medical device to be used in hospital procedures without the need to obtain a second device with a viable or operating RFID transponder.

A further advantage of the present disclosure allows the RFID transponder emulator to be used to store larger amounts of data than may be stored in a typical RFID transponder. This larger amount of data may be used for a variety of purposes, such as, updating the internal software of an electrosurgical generator, transferring of operating parameters, calibrating data or new operating mode definitions to an electrosurgical generator, transferring of graphical or textual information to an electrosurgical generator, transferring large amounts of data from an electrosurgical generator, such as log files, error files, calibration, status, clinical procedure, and performance data, and other pertinent and useful information.

The illustrated devices or methods described above may be implemented in software, hardware, firmware or combinations thereof. The processes and methods discussed herein need not be performed in the stated order. Multiple processes may be performed concurrently with each other. Furthermore, if desired, one or more of the above described processes may be optional or may be combined without departing from the scope of the present disclosure. Thus, the features and aspects of the present disclosure may be implemented in any suitable fashion by using any suitable software, firmware, and/or hardware.

In exemplary embodiments, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

The computers, computing devise, or processing devices may be operatively associated with the medical device according to the present disclosure. The software further directs the computer to modify the RFID transponders.

Additionally, the terms "software," "code," and "program" are used interchangeably and denote any plurality of binary values or any executable, interpreted or compiled code, which may be used by a computer or execution device to perform a task. This code or program may be written in any one of several known computer languages.

The term "computer" as used herein denotes any device, which stores, processes, routes, manipulates, or performs like operation on data. A "computer" may be incorporated within one or more transponder recognition and collection systems or servers to operate one or more processors to run the transponder recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A system comprising:
a plurality of medical devices each including a radio frequency identification (RFID) transponder storing a data set; and
an RFID transponder emulator storing a plurality of data sets, each of the plurality of data sets corresponding to the data set stored in each of the RFID transponders of the plurality of medical devices, the RFID transponder emulator configured to emulate, using the stored plurality of data sets, functionality of each of the RFID transponders of the plurality of medical devices, the RFID transponder emulator including a user interface for selecting a mode from a plurality of modes of operation and which of the RFID transponders to emulate.

2. The system according to claim 1, further comprising an RFID interrogation device configured to receive information emulated by the RFID transponder emulator.

3. The system according to claim 1, wherein the RFID transponders of each of the plurality of medical devices include data related to at least one of unique identifiers, digital signatures, authentication features, authorization features, anti-counterfeiting features, device usage management features, encrypted data, and unencrypted data.

4. The system according to claim 1, wherein the RFID transponder emulator includes an antenna, an analog front end (AFE), a processor, and a memory.

5. The system according to claim 4, wherein the AFE emulates radio frequency (RF) response of an RFID transponder included in each of the RFID transponders of the plurality of medical devices.

6. The system according to claim 5, wherein the memory stores information received from the RFID transponder emulator through the AFE and the processor processes information.

7. The system according to claim 1, wherein the RFID transponder emulator includes a display device for displaying the mode selected from the plurality of modes of operation.

8. The system according to claim 1, further comprising an electrosurgical generator configured to receive and process information collected, processed, and stored on the RFID transponder emulator.

9. The system according to claim 1, wherein the RFID transponder emulator is a passive, high-frequency (HF) RFID transponder emulator.

10. A radio frequency identification (RFID) network comprising:
a plurality of medical devices each including an RFID transponder storing a data set;
an RFID transponder emulator storing a plurality of data sets, each of the plurality of data sets corresponding to the data set stored in each of the RFID transponders of the plurality of medical devices, the RFID transponder emulator configured to emulate, using the stored plurality of data sets, functionality of each of the RFID transponders of the plurality of medical devices, the RFID transponder emulator including a user interface for selecting a mode from a plurality of modes of operation and which of the RFID transponders to emulate; and a plurality of RFID interrogation devices configured to operatively communicate with the RFID transponder emulator;

wherein the RFID transponder emulator is used for development, testing, evaluation, and validation of each of the plurality of RFID interrogation devices.

11. The RFID network according to claim 10, wherein the RFID transponder emulator includes an antenna, an analog front end (AFE), a processor, and a memory.

12. The RFID network according to claim 10, wherein the RFID transponder emulator includes:

a display device for displaying the mode selected from the plurality of modes of operation.

13. The RFID network according to claim 10, further comprising an electrosurgical generator configured to receive and process information collected, processed, and stored on the RFID transponder emulator.

14. A method of emulating a plurality of RFID transponders, the method comprising:

configuring an RFID transponder emulator to operate in a mode from a plurality of modes of operation and to emulate at least one RFID transponder of a plurality of RFID transponders, associated with a respective medical device of a plurality of medical devices;

emulating functionality of the at least one RFID transponder; and interfacing with the RFID transponder emulator through an RFID interrogation device to operatively communicate with the RFID transponder emulator.

15. The method according to claim 14, further comprising providing the RFID transponder emulator with a plurality of input controls for selection of the mode of the plurality of modes of operation.

16. The method according to claim 15, further comprising displaying the mode selected from the plurality of modes of operation on a display device.

17. The method according to claim 14, further comprising transmitting information collected, processed, and stored by the RFID transponder emulator to an electrosurgical generator.

18. The method according to claim 14, further comprising operatively communicating a plurality of RFID communication protocols from the RFID transponder emulator to imitate a behavior of a plurality of RFID transponders.

* * * * *